United States Patent [19]
Tam et al.

[11] Patent Number: 6,022,733
[45] Date of Patent: Feb. 8, 2000

[54] SIMULATED BIOLOGICAL DISSOLUTION AND ABSORPTION SYSTEM

[76] Inventors: Yun K. Tam, 2012 - 104A Street, Edmonton, Alberta T6J 5L8; Keith Edward Anderson, 94 Finch Crescent, St. Albert, Alberta T8N 1Y6, both of Canada

[21] Appl. No.: 08/982,692

[22] Filed: Dec. 2, 1997

[51] Int. Cl.[7] .................................................. C12M 3/00
[52] U.S. Cl. .................................... 435/287.1; 435/297.3; 435/297.4; 435/298.2
[58] Field of Search ............................ 435/287.1, 297.1, 435/297.2, 297.3, 297.4, 298.1, 298.2

[56] References Cited

U.S. PATENT DOCUMENTS

| | | | |
|---|---|---|---|
| 4,667,504 | 5/1987 | Hobson | 73/38 |
| 4,681,858 | 7/1987 | Chaudhari et al. | 436/165 |
| 5,026,650 | 6/1991 | Schwartz et al. | 435/286 |
| 5,153,131 | 10/1992 | Wolf et al. | 435/240.24 |
| 5,153,132 | 10/1992 | Goodwin et al. | 435/240.24 |
| 5,153,133 | 10/1992 | Schwartz et al. | 435/240.24 |
| 5,155,035 | 10/1992 | Schwartz et al. | 435/240.24 |
| 5,518,915 | 5/1996 | Naughton et al. | 435/240.243 |
| 5,525,305 | 6/1996 | Minekus et al. | 422/111 |
| 5,589,649 | 12/1996 | Brinker et al. | 73/866 |

FOREIGN PATENT DOCUMENTS

| | | |
|---|---|---|
| 2162165 | 4/1994 | Canada . |
| 2201159 | 9/1994 | Canada . |

OTHER PUBLICATIONS

Chiou, W.L., Determination of drug permeability in a flat or distended stirred intestine, Int. J. Clin. Pharm. Ther., 1994; 32(9):474–482.

Grundy et al., Nifedipine Gits In–Vivo/In–Vitro Correlation, Proc. Intern. Symp. Control Rel. Bioact. Mater., 1996;23:18–19.

Katori et al., Estimation of Agitation Intensity in the GI Tract in Humans and Dogs Based on in Vitro/in Vivo Correlation, 1995;12:237–243.

*Primary Examiner*—David A. Redding
*Attorney, Agent, or Firm*—Cushman Darby & Cushman Intelluctual Property Group of Pillsbury Madison & Sutro, LLP

[57] ABSTRACT

The invention relates to a system and method for assessing simulated biological dissolution of a pharmaceutical formulation and absorption of a pharmaceutically active compound therefrom. The system comprises a dissolution chamber and a cell culture chamber. Within the dissolution chamber, the dissolution profile of the pharmaceutical formulation (or drug) is determined. Within the cell culture chamber, the pharmaceutically active compound may be absorbed and transported by a cell monolayer. The cell culture chamber includes a tubular filter which is permeable to medium and capable of supporting the cell monolayer on its interior surface. Insertion of the filter into the cell culture chamber housing forms an apical chamber interior of the filter, and a basal chamber between the filter and the wall of the housing. The filter rotates about an axis within the housing substantially parallel to the direction of media flow through the cell culture chamber. The medium flowing from the dissolution chamber contains the pharmaceutical formulation and is provided to the apical chamber. The rate of appearance of the pharmaceutically active compound in the medium outflowing from the basal chamber may be analysed to determine absorption of the pharmaceutically active compound.

5 Claims, 3 Drawing Sheets

SIMULATED BIOLOGICAL DISSOLUTION AND ABSORPTION SYSTEM

The invention relates to a dissolution and absorption system and more specifically to a system and method for assessing simulated biological dissolution of a pharmaceutical formulation and absorption of a pharmaceutically active compound therefrom.

BACKGROUND OF THE INVENTION

Techniques for assessing dissolution of pharmaceutical formulations were originally introduced by regulatory authorities in the pharmaceutical industry in an attempt to characterize release profiles of formulations with low solubility in aqueous media. However, the growing demand for controlled use of pharmaceutical formulations has resulted in the adoption of dissolution testing for most formulations for quality control and regulatory purposes. Furthermore, dissolution testing is being used in the formulation development process in order to determine rate of release of the active compound from the formulation, and other parameters relating to formulation performance, to develop optimal dosage forms and to establish in vitro-in vivo correlations (IVIVC).

When assessing dissolution of a pharmaceutical formulation in an in vitro system, it is normally desirable to achieve high in vitro-in vivo correlation (IVIVC). An in vitro system producing data that closely correlates with dissolution and absorption data obtained in vivo would be beneficial in the pharmaceutical industry as a tool for various applications including dosage form development and scale-up, production scale-up, lot-to-lot bioequivalence testing, testing of new strengths, testing of minor formulation changes, testing after changes in the site of manufacture, and as a reference for bioequivalence requirements.

As dosage forms become more advanced, dissolution testing must become more rigorous to impart a fundamental understanding of how much of a pharmaceutically active compound is available at the absorption site(s) at specific times. Furthermore, establishing relationships between dosage form and availability of a pharmaceutically active compound at the absorption site(s) and systemic blood levels of a pharmaceutically active compound will allow investigators to optimize the in vivo performance of a pharmaceutically active compound through specialized delivery techniques.

Dissolution technology which allows determination of IVIVC for pharmaceutically active compounds which exhibit poor membrane permeability characteristics, which undergo extensive intestinal metabolism, or which require specialized transport systems for absorption has not yet been developed. Techniques for correlating in vitro and in vivo dissolution data have heretofore been limited to accounting for factors such as interactions with mucins, bile salts, digestive enzymes, food effects, ionic strength, and pH. Factors such as gastrointestinal transit of a dosage form may be accounted for by temporal displacement of the absorption and dissolution data. Discrepancies between in vitro and in vivo values of dissolution and absorption have previously been corrected for by transformation of data, such as by applying intestinal weighting functions, which transformations may not allow for physiological interpretation. There is currently a need for a system which combines dissolution technology with a biological intestinal absorption model, such as cell culture, for use in formulating and testing dosage forms of pharmaceutical formulations. Advantageously, such a system would more closely resemble the physiological system compared with existing dissolution methods.

Human intestinal epithelial cell culture has gained wide acceptance for delineating mechanisms of absorption of pharmaceutically active compounds. Conventional cell culture techniques allow for correlation of flux of a compound across an epithelial layer with passive transcellular or paracellular transport, carrier mediated transport, and active transport.

Actively absorbed compounds or those absorbed through carrier-mediated or energy requiring mechanisms usually have a saturable component to their absorption. Current cell culture techniques can delineate the details of absorption pathways as well as carrier affinity and capacity. Further, cell culture may be used to describe efflux systems, such as the p-glycoprotein mediated efflux system, which reduces the absorption of certain compounds. Intestinal metabolism of a compound may occur and will reduce the overall absorption of the compound. This information is currently used to explain discrepancies in IVIVC by transforming the kinetic models to include saturable Michaelis-Menton kinetics, or alternatively to include metabolic or efflux kinetics to improve IVIVC. Current cell culture techniques conducted in 2-dimensions across horizontal filters do not account for temporal displacement of a pharmaceutically active compound due to gastrointestinal transit and other in vivo conditions. Conventional cell culture techniques allow for interpretation of absorption by transformation of in vivo data, but do not yield adequate IVIVC, except in the assessment of passively absorbed compounds. Further, transport studies using cell culture describe the compound in solution, and thus do not account for dissolution or diffusion from a dosage form, or account for the effect of a formulation or dosage form on absorption of the compound of interest.

There is a need for the integrated assessment of in vitro dissolution of a pharmaceutical formulation and absorption of an active compound therefrom. These two parameters have conventionally been considered and assessed separately. In vivo, the appearance of a pharmaceutical compound in the blood stream results from inter alia the dissolution of the formulation and absorption of the compound. In the case of compounds which are passively absorbed, the relative rates of dissolution and absorption determine which is the rate-limiting factor in the appearance of a compound in the blood stream. With the advent of more complex dosage forms, especially for compounds and formulations which interact with epithelial surfaces for absorption (eg. bioadhesive systems), metabolism, or efflux (i.e. those not passively absorbed), more advanced systems are required to assess the formulation impact on dissolution and absorption. Advantageously, an integrated system of dissolution and absorption will provide improved IVIVC without the inconvenience of error associated with predictive models using transformed data.

Dissolution technology is known and described in, for example, U.S. Pat. No. 4,681,858 (Chaudhari et al.), which discloses a dissolution cell and method for determining the in vitro release of a pharmaceutically active compound from a dosage form, such as from a suppository. The dissolution cell allows for assessment of the rate of release of the compound of interest into the dissolution medium. Also, U.S. Pat. No. 5,589,649 (Brinker et al.) discloses a dissolution testing apparatus which incorporates a plurality of test vessels and uses heat and mechanical stirring to dissolve dosage forms in each test vessel.

Conventional cell culture methodologies incorporate flasks, plates or wells to grow cells or cell monolayers. These techniques incorporate agitation or turbulent mixing to ensure circulation of the medium to the growing cells. Other types of cell culture chambers have been developed. For example U.S. Pat. Nos. 5,026,650 and 5,153,133 (Schwartz et al.) disclose a bio-reactor consisting of a horizontally rotating cell culture system with a coaxial tubular oxygenator. Cell growth occurs on microcarrier beads suspended in media while the culture vessel rotates about a shaft, which provides continuous oxygenation through a membrane. U.S. Pat. No. 5,153,131 (Wolf et al.) discloses a horizontally rotating cell culture chamber with a dialysis membrane for exchanging cell waste products with fresh nutrients while cells are maintained in suspension. Employment of a horizontally rotating culture chamber, such as those described in U.S. Pat. Nos. 5,026,650, 5,153,133 and 5,153,131 provides good mixing of incubation media without agitation or turbulent mixing which can be damaging to cultured cells.

Conventional models used to assess absorption or permeability of a pharmaceutically active compound assume that no metabolism of the compound occurs within the gut wall (Chiou, Int. J. Clin. Pharm. Ther. 1994;32(9):474). However, the present invention could possibly be used to evaluate gut metabolism and the effect upon absorption of a compound. Additionally, conventional models assume that a compound, once absorbed, is immediately cleared from the basal side of the gut. This assumption does not account for conditions which may delay basal clearance. For example, anesthetics may decrease blood flow to the gut, thereby slowing basal drug clearance.

U.S. Pat. No. 5,518,915 (Naughton et al.) teaches a three dimensional mucosal cell and tissue culture system in which cells derived from a desired tissue are grown on a support matrix. The metabolism of, for example, a pharmaceutically active compound by the cells in this three-dimensional culture can be assessed. However, Naughton et al. does not incorporate dissolution of a pharmaceutical formulation prior to assessment of metabolism or absorption of a compound by the cultured cells.

U.S. Pat. No. 5,525,305 (Minekus et al.) discloses an in vitro model of the digestive tract. The system comprises tube-like chambers made of flexible material which are connected for the flow of gases or liquid therethrough. The contents of the chambers simulate gastric fluids and may include intestinal enzymes, acids, etc. This system is useful for in vitro assessment of digestion and exchange of low-molecular weight components through permeable membranes, but cannot assess biological parameters such as absorption across a membrane and does not incorporate cultured cells.

Canadian Patent Application No. 2,201,159 (Myers et al.) teaches an artificial liver apparatus and method which uses isolated hepatocytes which may be attached to inert carriers and suspended in cell culture medium to allow for purification of a biological fluid such as blood. As the biological fluid passes through the artificial liver apparatus and is exposed to hepatocytes, the hepatocytes can absorb and metabolize components of the biological fluid in a manner similar to the function of the liver in vivo. This system uses isolated cells as a model of in vivo hepatic metabolism but does not incorporate dissolution technology.

U.S. Pat. No. 4,667,504 (Hobson) discloses a flow-through device for determining the penetration rate of chemicals across a biological membrane in vitro. The apparatus comprises two chambers, one containing media including a test chemical, and the other containing media in which the test chemical appears when transported across the biological membrane which is suspended between the chambers. The media in each chamber may be sampled and analysed for concentration of the test chemical. However, this method does not incorporate dissolution methodology.

SUMMARY OF THE INVENTION

It is an object of the invention to provide an in vitro method which combines assessment of dissolution of a pharmaceutical formulation with assessment of the absorption of a pharmaceutically active compound therefrom.

According to the invention, there is provided a system for assessment of simulated biological dissolution of a pharmaceutical formulation and absorption of a pharmaceutically active compound therefrom, which system comprises:

a dissolution chamber for determining the dissolution profile of the pharmaceutical formulation in a medium to be supplied to the apical surface of a cell monolayer;

a cell culture chamber wherein absorption of the pharmaceutically active compound by the cell monolayer may occur, which cell culture chamber comprises:

i) a housing;

ii) a tubular filter which is permeable to medium and capable of supporting the cell monolayer on its interior surface; whereby insertion of the filter into the housing forms an apical chamber interior of the filter, and a basal chamber between the filter and the wall of the housing; and wherein the filter is rotatable about an axis within the housing substantially parallel to the direction of media flow through the basal and apical chambers, iii) means provided on said housing for the supply and outflow of basal medium to the basal chamber and apical medium to the apical chamber;

whereby the medium flowing from the dissolution chamber containing the pharmaceutical formulation is provided to the apical chamber, and the rate of appearance of the pharmaceutically active compound in the medium outflowing from the basal chamber may be analysed to determine absorption of the pharmaceutically active compound.

Rotation of the filter in this system may be controlled by a rotation control means located exterior to the housing or may be controlled by forces resulting from the flow of medium into the apical or basal chamber.

The system may additionally comprise an electrode within the apical chamber and an electrode within the basal chamber, which electrodes may be used to determine transepithelial electrical resistance across the cell monolayer. A flow-through dissolution system may be used as the dissolution chamber of the invention.

Additionally, the invention provides a method for determining simulated biological dissolution of a pharmaceutical formulation and absorption of a pharmaceutically active compound therefrom, comprising the steps of:

determining the dissolution profile of the pharmaceutical formulation in an apical medium; exposing the apical surface of a cell monolayer to the apical medium containing the pharmaceutical formulation; exposing the basal surface of the cell monolayer to a basal medium; and determining the rate of absorption of the pharmaceutically active compound from the apical medium by the cell monolayer.

The method of the invention may determine the rate of absorption of the pharmaceutically active compound by the cell monolayer on the basis of the rate of appearance of the active compound in the basal medium. To create sink conditions, the concentration of the pharmaceutically active compound in the basal medium may be maintained at 15% or less of the concentration in the apical medium. According to the invention, there is also provided a use of the above-noted method for determining the IVIVC of a pharmaceutically active formulation or dosage form.

The in vivo performance of a pharmaceutical formulation or the pharmaceutically active compound contained therein is dependent upon inter alia the solubility and stability of the formulation and the compound in the biological milieu, the biological disposition of the formulation and the compound, the release kinetics of compound from the formulation, the residence time of the compound at absorption and effector sites, and the transport of the compound across biological membranes, for example, the gastrointestinal epithelium. A compound may be transported across a biological membrane via simple diffusion processes such as passive transcellular or paracellular transport or via an energy driven process such as carrier mediated transport, facilitated transport, receptor mediated endocytosis, or any other active process. Transport across the gastrointestinal epithelium depends on inter alia the mass of available compound at the absorption site, the residence time at the absorption site, the surface area of the absorption site, the apparent permeability ($P_{app}$) across the epithelial membrane, and the diffusivity across the unstirred water layer surrounding the epithelial membrane. The formulation may affect any or all of these parameters to influence the absorption of the pharmaceutically active compound of interest.

A pharmaceutical formulation may be delivered in a variety of dosage forms with varying composition, shape, size, etc. Different dosage forms of a formulation also require dissolution testing to determine optimal parameters. Currently, the design of a dosage form is based in part on the principles of dissolution and diffusion theory. Diffusion is the process of mass transfer of individual molecules of a substance, brought about by random molecular motion in association with a concentration gradient. Diffusion can be described by solutions for Fick's first and second laws of thermodynamics. Fick's first law states the amount (M) of material flowing through a unit cross section (S) of a barrier per unit time (t) is known as the flux (J). Flux (J) is calculated as follows:

$$J = \frac{\delta M}{S \cdot \delta t} \quad \text{(I)}$$

Flux (J) is in turn proportional to the concentration gradient. The diffusion coefficient (D) of the diffusant, the concentration (C) of the diffusant and the distance (x) of movement perpendicular to the surface of the barrier, can be used to calculate flux (J) as follows:

$$J = -D\frac{\delta C}{\delta x} \quad \text{(II)}$$

Fick's second law states that the change in concentration with time in a particular region is proportional to the change in concentration gradient at that point in the system. Thus, the change in concentration over time is calculated as follows:

$$\frac{\delta C}{\delta t} = D\frac{\delta^2 C}{\delta x^2} = \frac{\delta^2 C}{\delta y^2} + \frac{\delta^2 C}{\delta z^2} \quad \text{(III)}$$

wherein x, y and z represent the distance of movement relative to the surface of the barrier.

Dissolution is the rate at which a solid formulation passes into solution. The Noyes-Whitney equation originally described the rate at which a solid dissolves in a solvent in simple terms as follows:

$$\frac{\delta C}{\delta t} = \frac{DA}{Vh}(C_s - C) \quad \text{(IV)}$$

wherein $\delta C/\delta t$ is the dissolution rate, D is the diffusion coefficient of the solute in solution, A is the surface area of exposed solid, h is the thickness of the diffusion layer, V is the volume of solution, $C_S$ is the solubility of the solute, and C is the concentration of solute at time t. Equations (I) to (IV) assist in predicting the behaviour of a pharmaceutical dosage form when placed in a biological environment. Diffusion and dissolution are intimately related, occurring simultaneously in a dosage form, resulting in systems which are controlled by one or both phenomenon. Dissolution testing allows for the determination of the quantity of a pharmaceutical formulation in solution and thus, the quantity of the pharmaceutically active compound available to be absorbed can be reproducibly determined. The end product of dissolution testing, therefore, is a kinetic representation of the dosage form, resulting from the dynamic interaction of the formulation, the pharmaceutically active compound contained therein, and the gastrointestinal environment.

Dosage forms of a formulation can range from simple immediate release, sustained release, pulsatile release, osmotic pumps, controlled release, targeted delivery, and many others, all of which are designed to control the available amount of the pharmaceutically active compound to be absorbed by the physiological system at a certain location or over time, conferring spatial and/or temporal selectivity. Dissolution of the dosage form may take place before, during, or after the active compound is released from the formulation, underscoring the dynamic interactions between the compound and the dosage form. A dosage form may be generally classified as a diffusion controlled system or a dissolution controlled system, depending on whether dissolution or diffusion is the rate limiting step for availability of the pharmaceutically active compound at the absorption site. However, some delivery systems may require physiological triggers or particular environmental conditions (e.g. pH changes), osmotic forces (e.g. osmotic pump), receptor-ligand binding, or other engineered dose dumping designs which will have more complex dissolution and absorption profiles.

The biological dissolution of a pharmaceutical formulation, the absorption of the pharmaceutically active compound therefrom, and the dosage form influence the in vivo performance of the active compound. Improved correlations have been accomplished by accounting for sink conditions and the Nernst or unstirred water layer surrounding a dosage form. Nernst layer effects can be minimized by adjusting stirring rates or optimizing the dissolution vessel assembly to ensure constant hydrodynamic conditions surrounding a dosage form. As described by the Noyes-Whitney equation (IV), a concentration gradient ($\delta C/\delta t$) influences dissolution ($C_s$-C). Sink conditions, wherein C <10–15% of $C_S$, are desirable in some cases to minimize the influence of concentration gradient on dissolution. Since $C_S$ is a constant for a pharmaceutically active compound under certain conditions, for low solubility compounds the sink condition may be achieved by decreasing C via increasing the volume of media or depleting the media of compound. Depletion of a compound from the media has previously been achieved through use of solid phase adsorbents, partitioning of the compound into a second organic phase, or transport across a membrane. Alternatively, $C_S$ has previously been increased through addition of organic co-solvents, surfactants, and co-solubilizers, although the physiologic relevance of these methodologies remains in question.

The most popular cell line for study of intestinal transport is the Caco-2 line, a transformed colonic cell line of oncogenic origin which spontaneously differentiates when cultured. Caco-2 cells express many characteristics of human small intestinal enterocytes including brush-border enzymes; folate and cyanocobalamin receptors; p-glycoprotein efflux system; sodium, potassium, phosphate, and proton pumps; hexose transporters; and carrier proteins for bile-salts and di-, or tri-peptides. The HT-29 cell line is a mucous secreting cell line which expresses characteristics similar to intestinal goblet cells. The T-84 colonic cell line has high electrical resistance and expresses characteristics similar to the large bowel. Transport of pharmaceutically active compounds by these and other cell culture lines possessing characteristics similar to human intestinal cells can be used to determine the biological availability of orally delivered dosage forms of a pharmaceutical formulation containing an active compound.

Various other epithelial cell types may be used with the invention. Any cell line capable of forming a monolayer may be employed. For example, in addition to the aforementioned intestinal and colonic cell lines, the MDCK (kidney cell) line may be used. Epithelial cell lines may be used which are involved in blood-brain barrier, blood-urine, blood-air (alveolar cell lines), blood-dermis, blood-hepatocyte, or blood-corneocyte (eye) interfaces or at any other interface between the blood central compartment and metabolic/clearance organs, depending on the information required. The cell lines which may be used with this invention include co-cultures, cell lines with point mutations, or any further advances in cell culture technology which may allow the use of non-transformed cell lines derived from human tissue or tissue from other mammalian species. Depending on the site of absorption of a pharmaceutical compound, different cell lines may be used. If the renal clearance of a compound is the research question to be addressed, a renal cell line could be employed. Additionally, hepatic metabolism could be assessed using a hepatic cell line.

For passively absorbed compounds, a relatively high IVIVC can be achieved by rank-ordering compounds by their oil-water partition coefficient (log $K_{O/W}$). $K_{O/W}$ is an equilibrium distribution coefficient and can be calculated as follows:

$$K_{O/W} = C_O/C_W \quad (V)$$

wherein $C_O$ is the concentration of the compound in oil (usually n-octanol) and $C_W$ is the concentration of the compound in water in a system at equilibrium at a specified temperature and pressure. The equilibrium distribution coefficient of a compound is an indicator of the hydrophobicity of the compound. The oil phase may be likened to the lipid membrane of a cell, and thus a higher $K_{O/W}$ coefficient indicates a higher rate of absorption. A conventionally determined IVIVC is less relevant for compounds with a log $K_{O/W}$ greater than 3.5 due to solubility problems. Also, a hydrophillic compound (i.e. low $K_{O/W}$) with a molecular weight less than the paracellular molecular size restriction (400–800 daltons) will have a higher absorption rate than that predicted by these simple models.

BRIEF DESCRIPTION OF THE DRAWINGS

Embodiments of the invention will now be described, by way of example, with reference to the accompanying drawings, wherein.

DETAILED DESCRIPTION OF THE PREFERRED EMBODIMENTS

Figure 1:
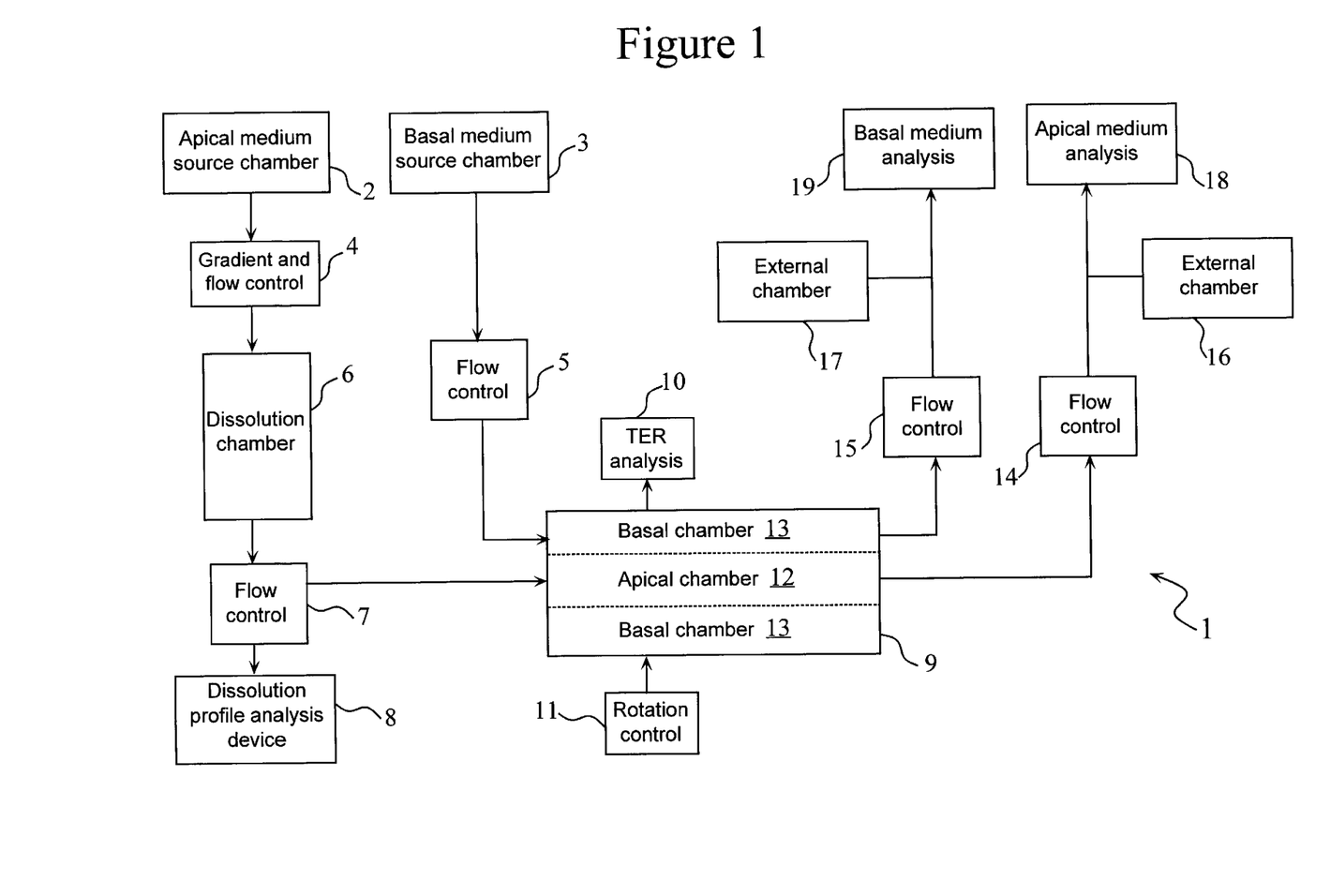
FIG. 1 is a flow chart of one embodiment of a simulated biological dissolution and absorption system.

The flow chart of FIG. 1 schematically illustrates a simulated biological dissolution and absorption system (1) according to a preferred embodiment of the invention. Medium is provided from an apical medium source chamber (2) to a dissolution chamber (6) via a means for gradient and flow control (4). The means for gradient and flow control may be any known in the art, such as a peristaltic pump. The apical medium source chamber (2) can control such parameters as the temperature and $pCO_2$. The gradient and flow control means (4) can be used to change flow or other conditions in the apical medium prior to introduction into the dissolution chamber (6). For example, conditions such as pH, osmolarity, bile salt or lipid content of the apical medium, can be altered prior to introduction of the medium into the dissolution chamber (6). Parameters such as pH and osmolarity may be measured by the gradient and flow control means (4). Numerous variations in the apical medium can be introduced prior to determination of dissolution. In a preferred embodiment, a plurality of apical media of varying composition are provided to the dissolution chamber (6) from the apical medium source chamber (2).

The apical medium is formulated to simulate certain aspects of the luminal contents of the intestinal tract, and is maintained at about 37.0±0.5° C. The pH of the apical medium will preferably range from 1 to 7, depending upon which aspects of the intestinal luminal contents it is desired to simulate. The apical medium will preferably include such components as bile salts, mucins, gastric acids, or nutrients such as amino acids, lipids or carbohydrates. Apical medium is provided to the dissolution chamber (6) for determining the dissolution profile of the pharmaceutical compound of interest, and for dissolution of the compound therein prior to providing the media to the apical chamber (12) of the cell culture chamber (9).

The basal medium, which flows to the basal chamber (13) of the cell culture chamber (9), may be of any type used to support cultured cells, and may comprise such ingredients as growth media, sera, buffers, minerals, nutrients, hormones, growth factors, and antibiotics/antifungals. In one embodiment, the basal medium will be oxygenated, will contain about 5% $CO_2$, and will be maintained at about 37.5° C. The temperature could be altered to investigate thermal effects on absorption rate, and $CO_2$ concentrations may be altered as required.

A basal medium source chamber (3), which may control temperature and $pCO_2$ of the basal medium, provides basal medium to the basal medium flow inlet (21) of the basal chamber (13) via an automated flow control means (5). The apical and basal media are supplied to the apical and basal chambers (12) and (13), respectively, on an ongoing basis so that there is a constant flow of medium during the determination of absorption of the pharmaceutically active compound of interest.

In the dissolution chamber (6), a dosage form of a pharmaceutical formulation containing a pharmaceutically active compound of interest is dissolved in apical medium, according to any known type of dissolution technology. The mixing rate in the dissolution chamber (6) influences the unstirred water layer surrounding the dosage form, and thus is under automated control. Once dissolution of the formulation into the apical medium has occurred, the medium flows out of the dissolution chamber (6) to a flow control means (7). The flow control means (7) splits the medium outflowing from the dissolution chamber (6) in order to regulate the flow entering the cell culture chamber (9). If dissolution leads to a large volume of apical medium containing the pharmaceutical formulation, only a portion thereof will enter the cell culture chamber (9) to maintain a standard flow rate and preventing excess shear stress on the cell monolayer within the cell culture chamber (9).

The flow control means (7) also shunts apical medium from the dissolution chamber (6) to a dissolution profile analysis device (8) which analyses the quantity of the pharmaceutical formulation dissolved or suspended in the apical medium leaving the dissolution chamber (6). A dissolution profile analysis device (8) according to any available methodology may be used to determine the dissolution profile of the pharmaceutical compound of interest in the medium outflowing from the dissolution chamber (6).

A filtration device may be incorporated into the dissolution chamber (6) to control the size of the particles leaving the dissolution chamber. It may be desirable to have particles of the dosage form remaining in the apical media to be supplied to the apical region (12), to obtain information regarding absorption of such particles.

Prior to flowing into the cell culture chamber (9), the concentration of various components of the apical medium and the basal medium are known. The dissolution profile of the apical medium is assessed after the addition of the pharmaceutically active compound in the dissolution chamber (6). Sampling and analysis of both the apical and basal media after the media have flowed through the cell culture chamber (9) using any appropriate method of analysis.

The dissolution chamber (6) may employ any available type of dissolution technology. Expediently, the dissolution chamber is of a flow-through design with laminar or turbulent flow to ensure good mixing (Moller, Pharmaceutical Industry 1983;45:617–622). Other types of dissolution technology which may be employed include surfactant or organic co-solvent addition (Abrahamsson et al., Pharmaceutical Research 1994;1 1:1093–7) and a two-phase system, such as an aqueous/organic phase method (Grundy et al., Proc. Intern. Symp. Control Rel. Bioact. Mater., 1996;23, Controlled Release Society, Inc., Baltimore, Md., August 21–22). Any available solubilizing technique may be employed to induce sink conditions as required.

The SOTAX™ systems (SOTAX Corporation, Richmond, Va.) are examples of currently available dissolution technology. The SOTAX AT 7™ dissolution testing apparatus meets current USP testing guidelines and has been adapted for automation of routine sequences. The SOTAX MEDIUM CHANGE™ system accommodates singe or multiple changes of media, and can be adapted for full automation. SOTAX SystemPlus EE™ provides dissolution software for analysis of dissolution data and production of a dissolution profile.

The apical medium is delivered from the dissolution chamber (6) via a flow control means (7) to the apical region (12) of the cell culture chamber (9). The flow control means (7) regulates the flow of apical media into the apical region (12) of the cell culture chamber (9). This flow may be fully automated to allow the result of the dissolution profile to determine flow rate into the apical chamber.

Figure 2:
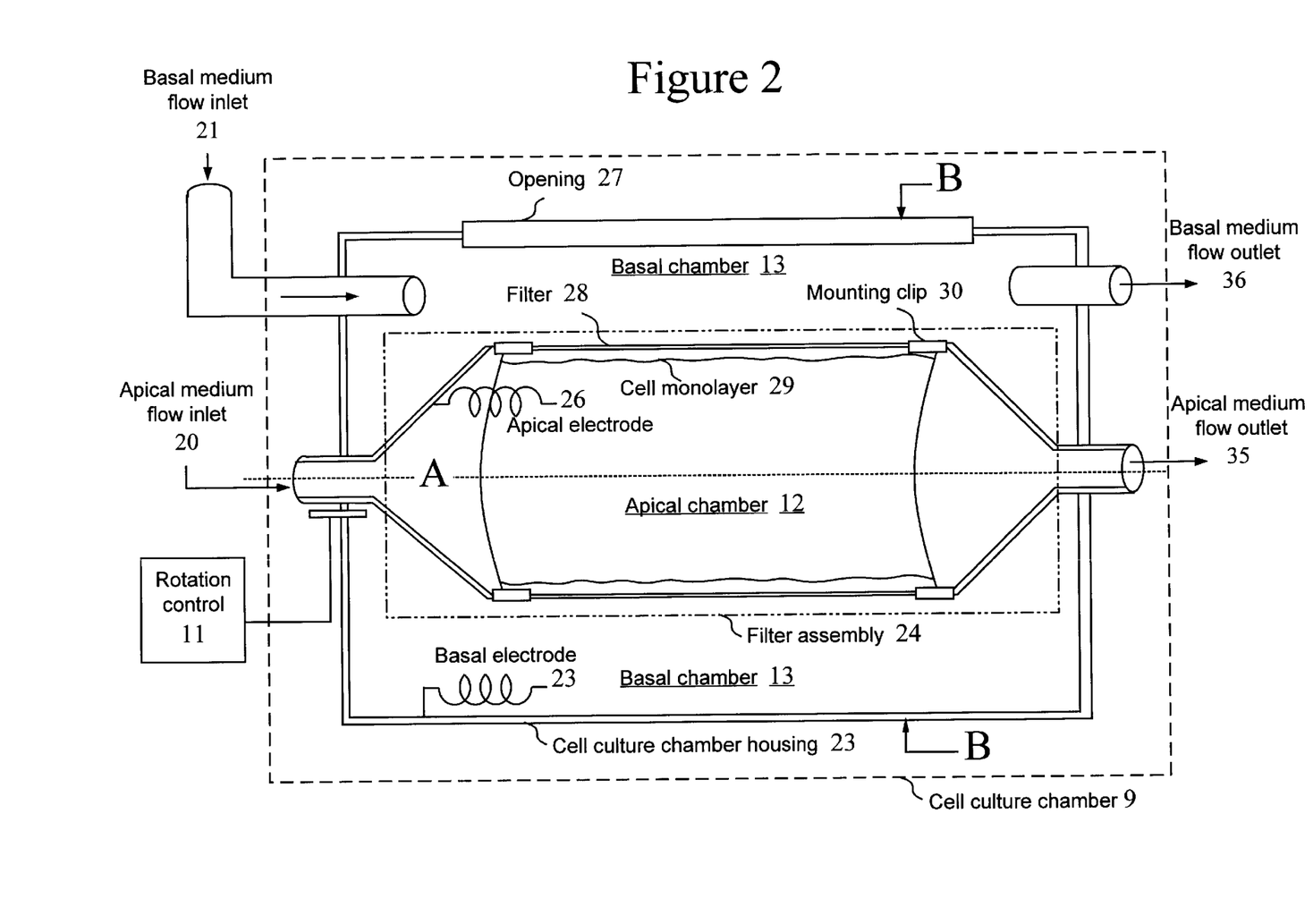
FIG. 2 is a schematic representation of the cell culture chamber of the simulated biological dissolution and absorption system of FIG. 1.

As illustrated in FIG. 1, and shown in detail in FIG. 2, the cell culture chamber (9) consists of the cell culture chamber housing (23) and the filter assembly (24). Insertion of the filter (28) into the cell culture chamber housing (23) partitions the cell culture chamber into the apical chamber (12) on the interior side of the filter (28), and the basal chamber (13), which surrounds the filter (28). The apical chamber (12) and the basal chamber (13) are thus distinct chambers through which media flow. Thus, the basal surface of the cell monolayer (29) is exposed to basal medium through the filter (28) which is permeable to media. The apical surface of the cell monolayer (29) is exposed to the apical medium.

Transepithelial electrical resistance (TER) analysis means (10) may be used to determine the viability or integrity of the cell monolayer within the cell culture chamber (9) by measuring resistance of the cell monolayer upon application of a voltage across electrodes on either side of the monolayer.

As illustrated in FIG. 2, an apical electrode (26) is preferably located in the apical chamber (12) and a basal electrode (25) is located in the basal chamber (13) for measurement of transepithelial electrical resistance as an indicator of cell viability in the monolayer (29). Transepithelial electrical resistance measures the integrity of the tight junctions between cells. High resistance indicates a confluent monolayer. Additionally, any acceptable measurement of cell viability may also be used to verify viability of cells in the cell monolayer (29). Other markers such as PEG, mannitol or inulin passage through tight junctions to indicate paracellular transport may also be used.

The filter assembly (24) comprises a filter (28) which is held in place by mounting clips (30) between the flow inlet (20) and the flow outlet (35). Rotation of the filter assembly (24) within the cell culture chamber (9) is controlled by a rotation control means (11), which in a preferred embodiment is motorized and external to the cell culture chamber (9). Rotation of the filter ensures good mixing and minimizes the unstirred water layer adjacent to the cell monolayer.

In a preferred embodiment, the filter assembly (24) is rotated by a rotation control means (11), which is a motor located at one end of the cell culture chamber housing (23). As shown in FIG. 2, the rotation control means (11) is linked to the filter assembly (24) and thus allows rotation of the filter assembly (24) about a horizontal axis (A) within the cell culture chamber housing (23). Rotation of the filter (28) and thus rotation of the cell monolayer (29) ensures good mixing of the media, which reduces the size of the unstirred water layer adjacent to the apical surface of the cell monolayer (29). Thus, contact of the pharmaceutically active compound and nutrients in the apical medium with the cell monolayer (29) is enhanced.

Alternatively, to cause rotation of the filter assembly (24) about the axis (A), the flow rate of the apical or basal medium into the cell culture chamber (9) may be adjusted so as to cause such rotation by inflow of medium, instead of using an external rotation control means.

The apical medium, containing the pharmaceutical formulation, and the basal medium flow through the apical and basal chambers (12) and (13), respectively, of the cell culture chamber (9) at rates controlled by flow control means (7) and (5). Once the media have traversed the cell culture chamber (9), each medium flows to a further flow control means (14) and (15), respectively. Flow control means (14) and (15) serve as entry ports for apical and basal media to the apical and basal medium analysis means (18) and (19), respectively.

Prior to entry of the apical and basal media into the respective analysis means (18) and (19), media may flow to external chambers (16) and (17) which serve as collection devices for excess media, or which may dilute the media or derivatize the compound of interest within the media, or perform other manipulations of the media which may be required for analysis. Medium analysis means (18) and (19) may be comprised of any device of the required sensitivity. Detection of low levels of the compound of interest in the basal medium would require highly sensitive basal media analysis means.

Figure 3:
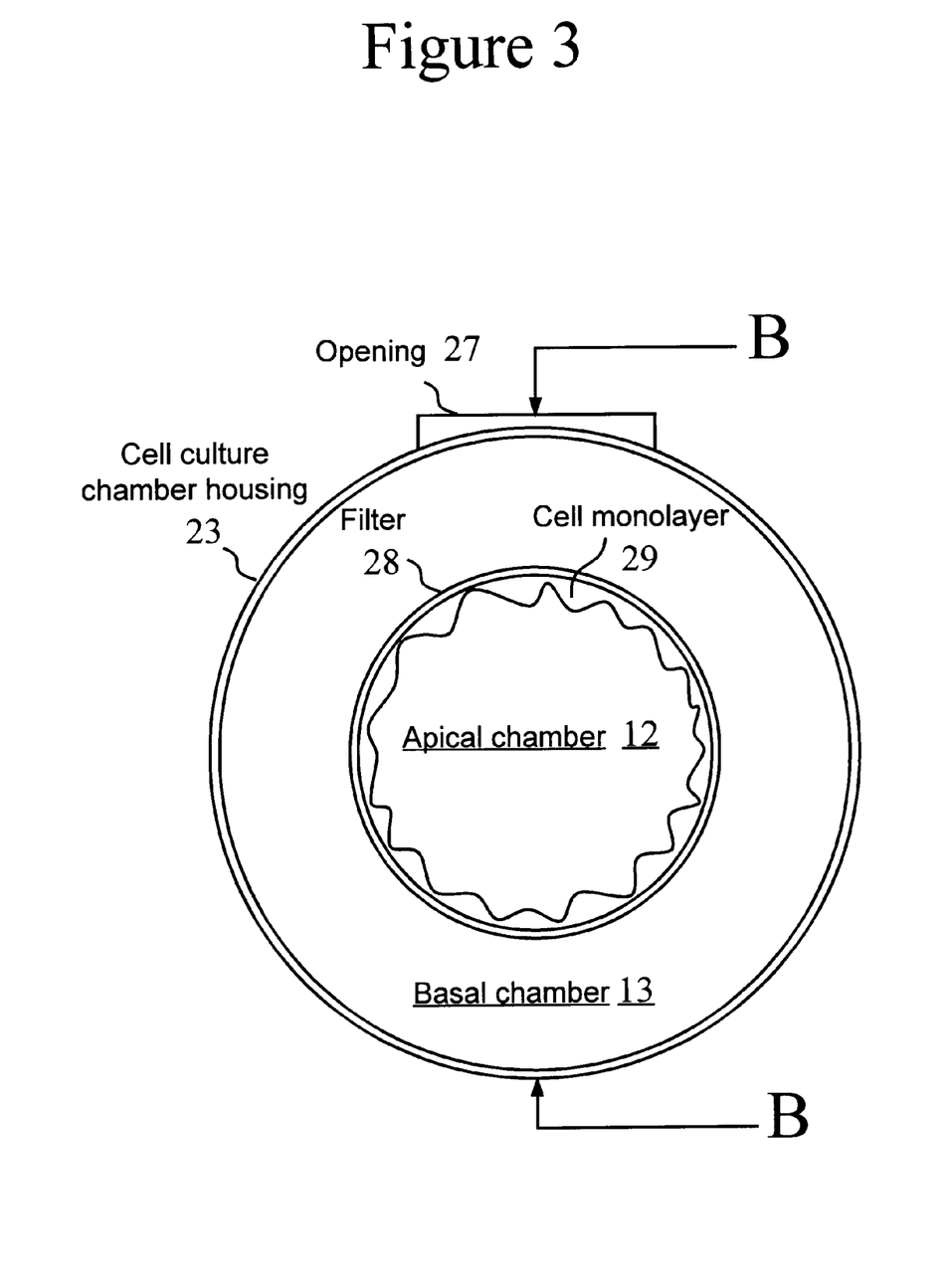
FIG. 3 is a schematic representation of the cell culture chamber of FIG. 2 in cross section along B—B of FIG. 2.

FIG. 2 illustrates the cell culture chamber (9) according to the embodiment of the invention represented in FIG. 1. FIG. 3 shows this embodiment as shown in section along the line B—B of FIG. 2. The apical medium, to which the apical surface of a cell monolayer (29) will be exposed, and basal medium, to which the basal surface of a cell monolayer (29) will be exposed are provided to the cell culture chamber via the apical medium flow inlet (20) and the basal media flow inlet (21).

Within the cell culture chamber (9) is a rotatable filter assembly (24) containing a tubular filter (28) capable of supporting a cell monolayer (29) on the inner surface thereof. The cells of the monolayer are polarized so that the basal cell surface is adjacent to the filter (28). The apical cell surface, corresponding to the luminal aspect of the gastrointestinal tract, faces the inner lumen of the filter (28). The filter (28) is removably inserted into the cell culture chamber housing (23) so that an apical chamber (12) and a basal chamber (13) are formed. The apical and basal media flow through the apical and basal chambers (12) and (13), respectively.

In the embodiment of the invention shown in FIG. 2, the filter (28) containing the monolayer of cells (29) is inserted into the cell culture chamber housing (23) via an opening (27) in the housing. Mounting clips (30) in the rotatable filter assembly (24) are used to keep the filter (28) in place. The length of the mounting clips (30) is equivalent to the length of supports which may be used to secure the filter in a primary culture assembly, which is discussed in further detail below. Cells do not grow on the portion of the filter rendered inaccessible by the clips.

The system is designed so that flow rate through the apical chamber (12) simulates gastrointestinal flow, and is not disruptive to the cell monolayer (29). Flow rates through the human gastrointestinal tract vary depending on parameters such as the radius of the intestinal segment, peristaltic contraction, and pendular movement of intestinal villi. Luminal flow rates in the human gastrointestinal tract are estimated to range from about 3 to about 18 mL/minute, based on a luminal radius of 1.3 cm (Chiou, Int. J. Clin. Pharm. Ther. 1994;32(9):474). The flow rate of the apical medium through the apical chamber (12) according to the invention is preferably maintained below 20 mL/minute. Currently, standard flow rates for flow-through dissolution methods range from 8 to 15 mL/minute. The flow will vary according to the diameter or surface area of the filter.

A higher flow rate of apical and basal media through the apical and basal chambers (12) and (13) may be required, for example, to ensure sink conditions, and thus a flow rate of up to 50 mL/minute may be employed. Higher flow rates through the basal chamber (13) are only minorly disruptive to the cell monolayer (29), since the filter (28) separates the monolayer (29) from the basal chamber (13) and thus acts a barrier to any turbulence which may be caused in the basal chamber (13) due to flow of medium therethrough. As the diameter or surface area of the filter (28) is reduced, the flow rates of both the apical and basal media through the cell culture chamber (9) may also be reduced, with a view to establishing conditions which are physiologically relevant.

Temperature control of the cell culture chamber (9) can influence temperature of the basal medium, to which the basal surface of the cell monolayer (29) is exposed. The apical surface of the cell monolayer (29) is exposed to the apical medium, the temperature of which may be controlled by means external to the cell culture chamber (9). The rotation control means (11), in this case, a motor external to the cell culture chamber, controls the rotational speed of the filter assembly (22). Preferably, the rotational speed will not exceed 100 rpm.

The apical medium flow inlet (20) is located at one end of the apical chamber (12) and is positioned co-axial to the axis of rotation (A) of the filter assembly (24). The apical medium flow outlet (35) is disposed at the other end of the apical chamber (12), co-axial to the axis of rotation (A) of the filter assembly (24). Thus, the flow of apical medium occurs parallel to the axis of rotation (A) of the filter assembly (24). Medium obtained from the flow outlet (36) can then undergo analysis for the concentration of the pharmaceutically active compound of interest or presence of metabolites of the compound of interest. The invention may also be used to assess metabolite formation from the pharmaceutically active compound of interest across the monolayer (29) or may be used to assess the amount of any component of the pharmaceutical formulation transported across the monolayer (29).

The basal medium flow inlet (21) is located at one end of the basal chamber (13), and the basal medium flow outlet (36) is located at the axially opposed end of the basal chamber (13). Thus the flow of basal medium occurs in a direction parallel to the axis of rotation (A) of the filter assembly (24). Medium obtained from the basal medium flow outlet (36) can then undergo analysis.

Control of the flow rate into the basal chamber (13) can be used to achieve sink conditions across the cell monolayer (29). The concentration of the pharmaceutically active compound in the basal medium may be maintained at 15% or less of the concentration in the apical medium at all times by adjusting the flow rate of the basal medium into the basal chamber (13). If absorption rate increases across the cell monolayer (29), flow rate of the basal medium can be increased to ensure that the concentration gradient does not limit absorption by the monolayer (29).

Parameters such as flow rates of media through the apical (12) and basal (13) chambers, composition of the apical and basal media, media oxygenation, and rotational speed of the filter assembly can be modified to optimize conditions for a particular application.

Apical and basal media flow out of the cell culture chamber via the apical and basal medium flow outlets (35)

and (36), respectively. Analysis of the apical medium both before and after flow through the cell culture chamber (9), and determination of the quantity of the compound of interest appearing in the basal medium after flow through the cell culture chamber (9), allow for accurate determination of absorption of the active compound by the cell monolayer (29) which can then be related to the dissolution of a tested formulation to determine the simulated biological dissolution of the formulation and absorption of the compound of interest therefrom.

Thus, the parameters of dissolution and absorption can be determined within a single system to provide a measurement of the in vitro performance of a dosage form of a pharmaceutical formulation.

In one embodiment of the invention, sink conditions across the cell monolayer (29) are adhered to and the flow of the basal medium is adjusted so that, within the cell culture chamber (9), the concentration of the pharmaceutically active compound of interest in the basal chamber (13) does not exceed 15% of the concentration in the apical chamber (12). According to the invention, this sink condition is preferably maintained across the cell monolayer (29). Sink conditions between the basal (13) and apical (12) chambers of the cell culture chamber (9) ensure that transport and other aspects of absorption or metabolism are unaffected by excessive concentration of the pharmaceutically active compound.

Additionally, it is also optional that sink conditions are maintained in the apical medium so that the concentration of the pharmaceutically active compound does not exceed 10 to 15% of the saturated solubility concentration. This dissolution gradient is not always required to accurately assess simulated biological dissolution and absorption using the system and method of the invention.

To accompany the system of the present invention, cells from an intestinal cell line, such as Caco-2 cells, are grown on a filter in a primary culture assembly for use with the invention. A filter is inserted into a primary culture assembly housing and is maintained in place with supports found at each end of the filter which are preferably the same depth as the mounting clips in the cell culture chamber, to ensure that the cells do not grow to the ends of the filter. The filter may be rotatable along a horizontal axis. Any culture method may be employed which allows a confluent monolayer of cells to adhere to the inner side of the filter. In this particular embodiment, cell inoculum is inserted in the luminal aspect region of the filter within the primary culture assembly which is then immersed in culture medium and placed in an incubator to allow development of the cell monolayer. The primary culture assembly may vary in size as necessary for various filter sizes. The primary culture assembly housing may be a single or multi-well plate, or any other appropriate vessel which can support the growth of a monolayer on a filter inserted therein. The filter is preferably disposable, and in the present embodiment, is preferably from 0.5 to 2 cm in diameter. The use of smaller sized filters for automated multiple sampling systems is also anticipated by the invention.

Cultured cells are grown on the inner surface of the tubular filter (28), and are polarized so that the apical surface of the cell monolayer (29) facing the interior portion of the filter, and the basal (basolateral membrane) surface of the monolayer is adjacent to the filter (28), facing outward. Alternatively, cells may also be grown on flat filter sheets in a primary culture assembly and the filter sheets may then be formed into a tubular shape prior to insertion into the cell culture chamber.

The filter (28) is preferably comprised of nitrocellulose, polycarbonate or any other inert material on which cells may be cultured. The filter is of a defined pore size and surface area, excluding the area covered by the mounting clips (30). Once a cell monolayer (29) has developed on the filter (28), the filter is removed from the primary culture assembly and is inserted into the cell culture chamber (9) of the simulated biological dissolution and absorption system.

Porous permeable membrane filters or supports upon which cultured cells can grow are readily available. For example, Transwell™ Permeable Supports are available from Corning Costar Corporation (Cambridge, Mass.). Transwell™ Permeable Supports specifically allow convenient independent access to apical and basal plasma membranes when cells are grown in a monolayer.

According to the system and method of the invention, parameters such as mechanical stresses, intestinal distension, shear force, interspecies variability, etc. can be addressed by adjusting flow rates of the media through the cell culture chamber. Also, basal flow could be adjusted for sink conditions, i.e.—for low solubility compounds, higher flow rates may be necessary. The high end of the range for basal flow may mimic human physiology for blood flow.

The system of the present invention may incorporate different types of flow through the cell culture chamber, such as laminar, peristaltic, tortuous, etc. to simulate gastrointestinal distension and transit. A pendular motion may be created by rocking the cell culture chamber. These and other manipulations of the conditions within the cell culture chamber may be incorporated to simulate gastrointestinal transit.

In an embodiment of the invention, the flow of media entering the cell culture chamber could be determined by a valve allowing varying proportions of the dissolution chamber flow into the apical medium flow inlet, so as to control the shear force on the surface of the cell monolayer. According to one embodiment, the valve radius may be extensible from between 0 to 1.3 cm, to allow for temporary cessation of flow (eg. when valve radius is 0 cm) or to regulate flow rate (eg. when valve radius of greater than 0 cm).

Additionally, according to the invention, the design may be automated, or reduced in size to allow for a plurality of simultaneous measurements using reduced quantities of media and cells. Simultaneous multiple unit testing thus allows for expedient assessment of simulated biological dissolution and absorption. Miniaturization of the system allows for a reduction in the required amount of solutions, solutes, cells, and other materials. The system may be used to assess the amount of permeation of a pharmaceutically active compound across the cell monolayer (29), active or passive transport of a compound by the cell monolayer, or metabolic conversion of a compound by the monolayer.

We claim:

1. A system for assessment of simulated biological dissolution of a pharmaceutical formulation and absorption of a pharmaceutically active compound therefrom, which system comprises:

a dissolution chamber containing a pharmaceutical formulation within a medium to be provided to the apical surface of a cell monolayer;

an analysis device in flow communication with the chamber for determining the dissolution profile of the pharmaceutical formulation;

a cell culture chamber wherein the absorption of the pharmaceutically active compound by the cell monolayer may occur, said cell chamber comprises:

i) a housing;

ii) a rotatable tubular filter which is permeable to medium and capable of supporting the cell monolayer on its interior surface, said filter positioned within said housing forming an apical chamber within the interior of the filter, and a basal chamber between the filter and the wall of the housing, said filter capable of rotation about an axis within the housing substantially parallel to the direction of media flow through the basal and apical chambers;

iii) means provided on said housing for the supply and outflow of basal medium to the basal chamber and apical medium to the apical chamber; and iv) means for analyzing the medium flowing out from the basal chamber;

whereby the medium flowing from the dissolution chamber containing the pharmaceutical formulation is provided to the apical chamber and the rate of appearance of the pharmaceutically active compound in the medium flowing out from the basal chamber is analyzed to determine absorption of the compound.

2. A system according to claim 1, whereby rotation of the filter is controlled by a rotation control means located exterior to said housing.

3. A system according to claim 1, whereby rotation of the filter is controlled by forces resulting from the flow of medium into the apical or basal chamber.

4. A system according to claim 1, additionally comprising an electrode within the apical chamber and an electrode within the basal chamber which electrodes may be used to determine transepithelial electrical resistance across the cell monolayer.

5. A system according to claim 1, wherein the dissolution chamber is a flow-through dissolution system.

* * * * *